(12) United States Patent
Rochat

(10) Patent No.: US 6,705,983 B1
(45) Date of Patent: Mar. 16, 2004

(54) COMPACT CENTRIFUGE DEVICE AND USE OF SAME

(75) Inventor: Jean-Denis Rochat, Genolier (CH)

(73) Assignee: Haemonetics Corporation, Braintree, MA (US)

( * ) Notice: Subject to any disclaimer, the term of this patent is extended or adjusted under 35 U.S.C. 154(b) by 0 days.

(21) Appl. No.: 09/958,467

(22) PCT Filed: Apr. 7, 2000

(86) PCT No.: PCT/IB00/00437

§ 371 (c)(1), (2), (4) Date: Jan. 17, 2002

(87) PCT Pub. No.: WO00/61295

PCT Pub. Date: Oct. 19, 2000

(30) Foreign Application Priority Data

Apr. 9, 1999 (EP) .............................................. 99810295

(51) Int. Cl.[7] ................................................. B04B 1/16
(52) U.S. Cl. ................................ 494/2; 494/10; 494/45
(58) Field of Search ................................ 494/2, 10, 18, 494/45, 84; 210/380.1, 781, 782

(56) References Cited

U.S. PATENT DOCUMENTS

| 3,586,413 | A | * | 6/1971 | Adams |
| 4,007,871 | A | | 2/1977 | Jones et al. |
| 4,109,854 | A | | 8/1978 | Brown |
| 4,344,560 | A | * | 8/1982 | Iriguchi et al. |
| 4,531,932 | A | * | 7/1985 | Luppi et al. |
| 5,160,310 | A | * | 11/1992 | Yhland |
| 5,690,602 | A | | 11/1997 | Brown et al. |

FOREIGN PATENT DOCUMENTS

| DE | 28 48 953 A1 | | 5/1980 |
| EP | 260034 | * | 3/1988 |
| EP | 0 526 869 A1 | | 2/1993 |
| FR | 2 468 374 | | 5/1981 |
| GB | 2 063 719 A | | 6/1981 |
| WO | WO 88/01907 | | 3/1988 |
| WO | WO 88/05690 | | 8/1988 |

* cited by examiner

Primary Examiner—Charles E. Cooley
(74) Attorney, Agent, or Firm—Bromberg & Sunstein LLP

(57) ABSTRACT

This device includes a centrifugal cup or bowl (2) rotating at the speed of $2\omega$ around its revolving axis, a separation chamber (3) connected to the center of this cup or bowl (3) by three channels (4, 5, 6) integral to three flexible tubes (4a, 5a, 6a) forming open loops driven at the speed of $\omega$ while their second respect extremities, coaxially located with respect to the first ones, are stationary. The radius and height of this cup or bowl (2) are between 25–50 mm, and 75 to 125% respectively of this radius; its angular speed $2\omega$ is >500 rad/sec to ensure a flow rate for the liquid to be centrifuged of at least 100 ml/min. The material and the dimensions of the tubes (4a, 5a, 6a) are chosen so that the traction force exerted on them is <0.7 N/mm$^2$, its elasticity module is <5 N/mm$^2$ and its rupturing resistance to alternate bending is higher than 1.5 N/mm$^2$.

22 Claims, 4 Drawing Sheets ant application Ser. No. PCT/IB00/00437, filed Apr. 7, 2000,
COMPACT CENTRIFUGE DEVICE AND USE OF SAME

CROSS-REFERENCES TO RELATED APPLICATIONS

This application claims priority from International patent application Ser. No. PCT/IB00/00437, filed Apr. 7, 2000, which further claims priority from European patent application 99810295.8, filed on Apr. 9, 1999.

FIELD FO THE INVENTION

This invention relates to centrifuge systems for the general processing of fluids and, more specifically, a centrifugal device for liquids, such as blood.

BACKGROUND OF THE INVENTION

A system, that permits connecting a rotating unit with a flexible tube or a cord, forming an open loop of which one extremity is integral during rotation with the axis of the rotating unit at a speed 2ω while the other extremity, coaxially located with respect to the first, is stationary and that the open loop is driven at a speed ω, causing a rotation of the flexible tube around its own axis at a speed −ω, thus eliminating any twisting of this flexible tube, is revealed in U.S. Pat. No. 3,586,413. This principle that permits eliminating any joint between the flexible tube and the rotating unit has been largely applied in a large number of centrifugal devices. Taking into account the speed of the rotating unit in a centrifuge, the flexible tube rotating on itself at the −ω speed is subject to a traction effort caused by the centrifugal force, to a bending stress caused by the rotation on itself of the portion of the tube forming the open loop at the −ω speed, as well as a temperature increase caused by the work of the viscous forces in the substance due to the aforementioned bending. However, in the case of centrifuging blood, the temperature rise must be <5° C.

Taking into account these various stresses has led to solutions that, use centrifugal units of a relatively flat form and of a diameter considerably higher than 200 mm, with the ω rotating speed generally situated around 200 rad/sec, with the latter in some cases going up to 400 rad/sec. This choice permits limiting the rotating speed, reducing the bending and traction stress on the flexible tube while obtaining an acceptable flow rate for the liquid. This choice, which has largely spread in the field of centrifuges for blood, obviously leads to a centrifugal rotor of a relatively large diameter. Such a centrifugal rotor, taking into account the centrifugal forces to which it is subjected and its large diameter, must be sized to withstand these efforts, resulting in a rotor that weighs several kilos, so that it no longer is economical to produce a rotor of this type in disposable form, like in the case of plasmapheresis for the purpose of collecting plasma.

As such, in U.S. Pat. No. 4,076,169, a disposable enclosure has been proposed for centrifuging a liquid that contains suspended particles such as blood. Since such a disposable enclosure would not withstand the centrifugal efforts, it is installed in a housing located inside a rotor consisting of two circular half-shells fitting into each other. Installation of the centrifugal enclosure in the rotor housing requires a disassembly and an assembly operation of the rotor, its opening and the installation of the centrifugal enclosure.

A solution of the same type is described in U.S. Pat. No. 4,010,894, in U.S. Pat. No. 4,834,890, in U.S. Pat. No. 4,934,995 as well as in U.S. Pat. No. 4,531,932. In all these separation devices, the disposable separation enclosure consists of a flexible bag located in a support rotor, involving handling that is considerably less easy than with a rigid component.

In other solutions, like the one described in U.S. Pat. No. 4,108,353, centrifugal enclosures are positioned on the rotor presenting positioning and securing components for these enclosures. Again, in this case, installation of these enclosures requires a certain number of movements that are delicate and time-consuming. Moreover, such a system requires the presence of several enclosures, even in number, for the centrifugal rotor to be balanced. Such a system is consequently not practical for centrifugation in line with taking blood.

The only rigid rotors proposed in the case of separating blood components through centrifuging are those described in U.S. Pat. No. 4,330,080, in U.S. Pat. No. 4,540,397 as well as in U.S. Pat. No. 5,350,514. Besides a separation enclosure in the form of a disk of more than 200 mm in diameter, the rotor includes a tubular body on which two ring-shaped guiding surfaces are arranged and, between them, a toothed ring to engage in a drive pinion.

Mounting and dismounting of this rotor requires removing one of the three guide rollers engaged with each of the ring-shaped surfaces of the rotor. Since during centrifugation these removable rollers must ensure retention of the rotor, locking devices for these rollers must be provided for. Replacing these disposable rotors represents a complex operation that must be done carefully, taking into account the danger that might represent the accidental separation of the rotor during centrifugation.

In addition to these problems, the dimensions and designs of these rotors result in heavy devices that are large and expensive and that are unfit for plasmapheresis in line with taking blood. If, in a therapeutic application, the price of a disposable rotor does not have a determining importance, this price is determining. But if the blood cells, such as erythrocytes that take a long time for the human body to produce could to be reinjected into the donor, and the latter could give blood more frequently. However, this can only be done at the same time that blood is being taken and, for that, separation enclosures are required that can be produced at a sufficiently low price and that can be exchanged easily and reliably.

SUMMARY OF THE INVENTION

The purpose of this invention is to remedy, at least partially, the abovementioned inconveniences.

In a first embodiment of the invention, there is provided a centrifugal device for liquids containing suspended particles, such as blood. The centrifugal device includes a centrifugal unit with a center and a rotation axis. A plurality of channels connects the center of the centrifugal unit to a peripheral separation chamber, each channel having a central extremity. A plurality of tubes have first and second extremities, with the central extremities of the respective channels attached to the first extremities of the tubes and the second extremities of the tubes being angularly stationary and coaxially located with respect to the rotating axis. First drive units turn the tubes around said rotating axis at an angular speed ω. Second drive units turn the centrifugal unit around said rotating axis at an angular speed 2ω. The centrifugal unit has a radius between 25 and 50 mm and a height between 75 and 125% of the radius.

In accordance with related embodiments of the invention, the centrifugal unit may be capable of rotating at an angular speed 2ω>500 rad/sec. Liquid introduced to the centrifugal unit may be capable of flowing at a rate of less than 100 mL/min. The tubes may be capable of withstanding a traction force of <0.7 N/mm$^2$, have an elasticity module of <5 N/mm$^2$, and have a rupture strength at alternate bending of higher than 1.5 N/mm$^2$. The centrifugal device may have the form of a bowl that includes a bottom part attached to a top part so as to form said separation chamber. The tubes may form open loops around the centrifugal unit and may be incorporated in one flexible tubular component. The diameter of a cross-section of the tubular component may not exceed 7 mm.

In accordance with further related embodiments of the invention, use of the device may include putting said liquid to be centrifuged under pressure (P) to produce a flow at a given rate. The degree of purity is measured for at least one of the centrifuged components. The proportion of the respective flow rates is regulated for the two components coming from centrifugation according to said degree of purity.

In accordance with another embodiment of the invention, a centrifugal unit includes a centrifugal component and a plurality of tubes. The unit is capable of turning around an axis to separate components of a liquid, such as blood. The plurality of tubes are incorporated into a single tubular component. The unit includes a base in the form of a disk. An external cylindrical wall and an internal cylindrical wall extends from the base so as to define a ring-shaped separation chamber among each other. A tubular housing almost extending coaxially to the rotating axis from the base receives an end of a tubular unit. A plurality of channels extend radially in the base of the centrifugal unit, with each channel providing communication between a respective tube of the tubular unit and the separation chamber. The centrifugal unit has a radius between 25 and 50 mm and a height between 75 and 125% of the radius.

In accordance with another embodiment of the invention, there is provided a device to centrifuge a liquid containing suspended particles, such as blood. The device includes a first drive component mounted to pivot around an axis, A second drive component is mounted to pivot coaxially with respect to the pivoting axis of the first drive. Devices drive the first and second drive components at a 2:1 ratio. A centrifugal unit coupled but removable to the first drive component has a tubular housing coaxially connected to the pivoting axis. The centrifugal unit has a radius between 25 and 50 mm and a height between 75 and 125% of the radius. A tubular component is coupled at a first extremity to the tubular connection housing of the centrifugal unit, and at a second extremity to the connecting tubular housing, and defines an axis that is coaxially located to said pivoting axis. The tubular component is joined at the second drive component to rotate. The tubular component further incorporates a plurality of tubes installed inside, with each tube having an elliptic cross-section to facilitate the rotation of the tubular component around the longitudinal axis.

The centrifugal device according to this invention permits dividing the weight of the centrifugal unit by about 5 with respect to the known disposable rigid units. This weight reduction that also permits having a more compact centrifugal unit, permits reducing the weight of the centrifugal device, reducing its size, while facilitating its handling. As such, this device offers a new field of application for this type of device, since it facilitates its transportation by virtue of its reduction in terms of weight and size; besides the known applications in a hospital setting, it can be used in blood collection vehicles and permit the re-injection of the donor's own erythrocytes.

BRIEF DESCRIPTION OF THE DRAWINGS

Other benefits of this centrifugal device will appear during the description that follows, using the attached drawing in which.

DETAILED DESCRIPTION OF SPECIFIC EMBODIMENTS

Figure 1:
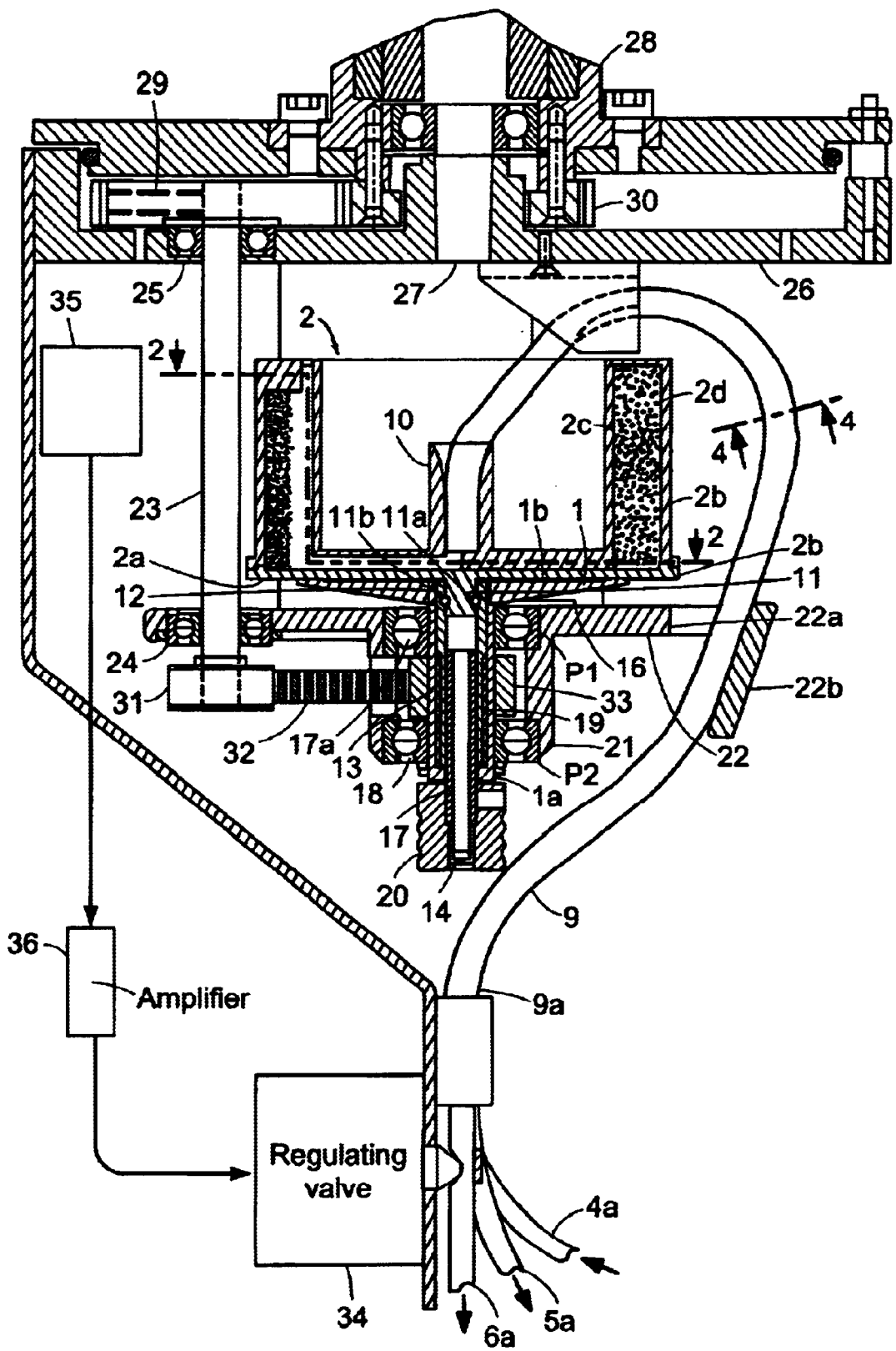
FIG. 1 is a sectional view of an elevation of this form of execution.
Figure 2:
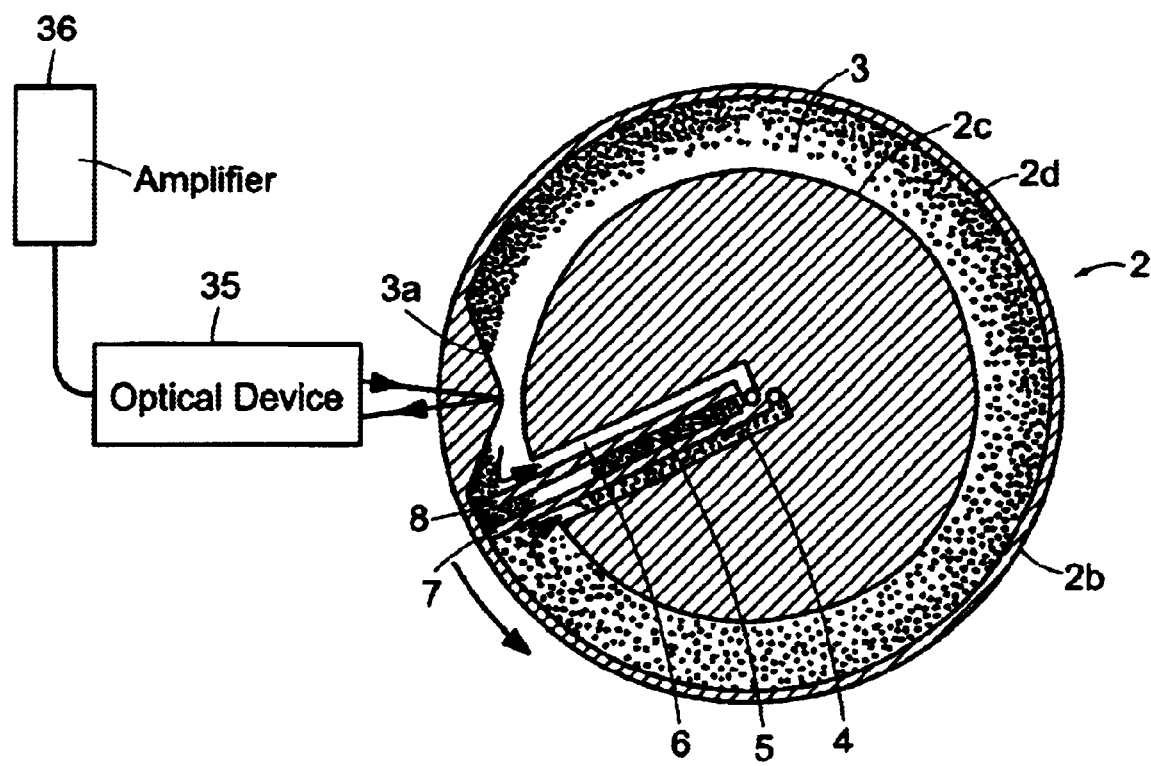
FIG. 2 is a partial sectional view, according to line II—II of FIG. 1.

The centrifugal device illustrated by FIG. 1, used among other things for plasmapheresis, includes a centrifugal rotor that has the form of a disk 1 arranged at the end of a tubular body 1a, mounted and pivoting in two ball bearings P1, P2. This centrifugal rotor 1 carries a disposable centrifugation cup or bowl 2, itself formed by joining two parts through welding or gluing, one at the bottom, formed by a disk 2a and the other on top 2b, showing two cylindrical and concentric side walls, one inside 2c and the other outside 2d between which is installed a ring-shaped separation enclosure 3 (FIGS. 1 and 2). Three radial channels 4, 5, 6 installed in top portion 2b of the centrifugal cup or bowl 2, connecting this ring-shaped separation enclosure 3 to the center of this cup or bowl 2. Channel 4 is the supply channel of the blood to be centrifuged. It has a partition 7 that joins side wall 2d of ring-shaped separation enclosure 3 while the other wall of this supply channel 4 ends at internal side wall 2c of this separation enclosure 3.

Partition 7 also serves to separate channel 4 from channel 5 used for recovering the blood cells, for which the other partition 8 ends at a certain distance of external side wall 2d of ring-shaped separation enclosure 3. This partition 8 thus separates channels 5 and 6 and makes them communicate, respectively, with the external portion of ring-shaped separation enclosure 3, in other words, the one where the blood cells are concentrated, from the one with the smallest density where the plasma is concentrated. Obviously, a subsequent separation of recovered blood cells is possible to separate the erythrocytes, the leukocytes and the platelets. For a variant of cup or bowl 2, one might also envisage having more than two outlet channels to obtain this separation.

Figure 4:
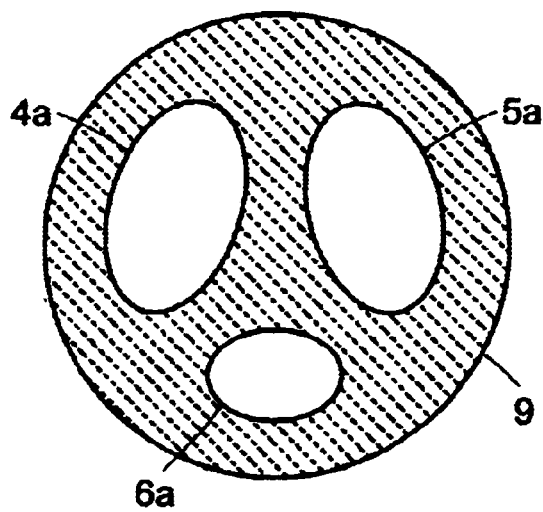
FIG. 4 is an enlarged sectional view according to line IV—IV of FIG. 1.

These three channels 4, 5, and 6 end at the center of cup or bowl 2 where they are connected to three tubes 4a, 5a and 6a respectively (FIG. 4) that are, preferably, arranged in parallel in one and the same flexible tubular component 9. The, portion of this tubular component 9, adjacent to its extremity connected to channels 4, 5, and 6 is held in a tubular housing 10 formed coaxially with the rotating axis of cup or bowl 2, on top portion 2b thereof. Me sections of the three tubes 4a, 5a and 6a are elliptical, with the large centerlines of these ellipses being tangential to at least one concentric circle with the longitudinal axis of tubular component 9. This orientation of the elliptical sections of tubes 4a, 5a, 6a facilitates the rotation of the tubular component around its longitudinal axis.

From the foregoing, it follows that the mobile part that is to be discarded after each use, consisting of three parts, cup or bowl 2, consisting of two parts 2a, 2b welded or glued together and tubular component 9. Moreover, this unit does not require any impervious seal. This unit is connected to, but can be removed from, the centrifugal rotor 1 in the manner described below.

The bottom of the disk that forms bottom part 2a of cup or bowl 2 carries a coupling element consisting of a cylindrical rod or tenon 11, comprising a semicircular groove 11a, adjacent to a truncated end 11b. This coupling rod 11 is engaged in a coupling element consisting of a ring 12, a coupling mechanism 13, with this ring and this coupling mechanism housed in the tubular portion 1a of rotor 1.

Coupling mechanism 13 includes a coupling device that, in this form of execution, consists of a ball ring 16 that is located at the inside end of the axial passage formed by ring 12 that is integral with tubular part 1a of rotor 1. A tubular piston 18 is mounted and sliding inside tubular part 1a. Its top extremity ends in a surface that has the form of a funnel 17a. This tubular piston 18 is pressed axially against the internal extremity of ring 12 by a helicoidal spring 18 comprised between one end of tubular part 1a of rotor 1 and a bearing surface of tubular piston 17. This axial pressure in the direction of ring 12 and funnel form 17a have the effect of exercising centripetal forces on ball ring 16 that presses them into groove 11a of coupling rod 11 of cup or bowl 2.

To prevent these balls from engaging in the axial opening of ring 12, during the removal of coupling rod 11, a second piston 14 is mounted and sliding inside tubular piston 17 and a second helicoidal spring 19 pushes it axially against the end of coupling unit 11.

According to a variant, ball ring 16 could be replaced by a split ring-shaped piano wire type spring, or by a coil spring that forms a toric spring, for which both extremities would then be brought together by funnel 17a under the pressure of helicoidal spring 18, thus reducing its diameter to keep it engaged in groove 11a of the coupling rod.

The external extremity of tubular piston 17 is integral with a grasping component 20 to permit an axial traction against the pressure of spring 18, to enable balls 16 to move towards the outside. Piston 14 subjected to the axial pressure of spring 19 can then eject cup or bowl 2 upwards and keep time balls 16 removed at the same.

As we can see in FIG. 1, to ensure a proper tightness of cup or bowl 2 on rotor 1, the top surface of the disk carrying this cup or bowl 2 shows a slight clearance 1b, that ensures good contact with the peripheral ring-shaped surface of this disk. Moreover, the axial position of groove 11a of the coupling rod 11 can be selected to find itself still partially in the axial passage of ring 12 so that the engagement of balls 16 in this groove 11a may induce a very slight sagging of the center at the bottom of cup or bowl 2 that permits the removal 1b of the disk of rotor 1, thus ensuring an adequate contact between this disk and cup or bowl 2 to ensure that the latter is being driven by friction.

Figure 3:
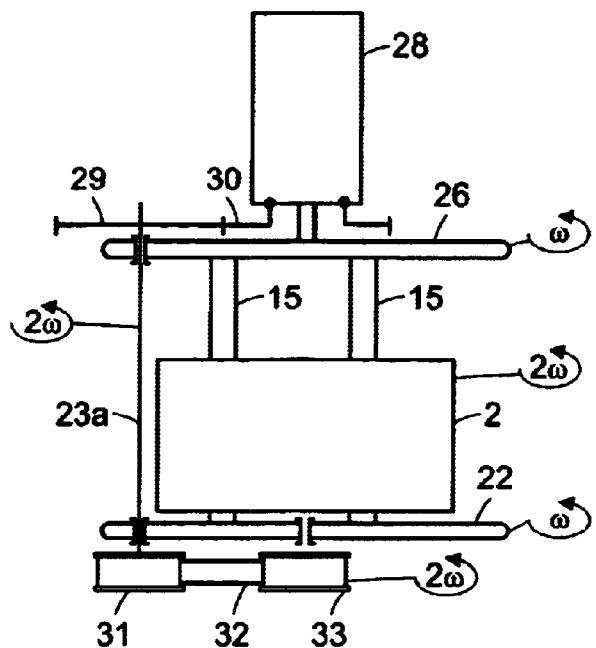
FIG. 3 is a schematic view of the kinematics of the drive mechanism.

Ball bearings P1, P2 of the tubular portion of the rotor are mounted in a support 21 secured to a tray 22, itself secured to a top disk 26 by four uprights 15, two of which are located behind cup or bowl 2 and which are visible on FIGS. 1 and 3; the other two are arranged symmetrically with respect to a drive shaft 23 parallel to the axis of rotor 1. Thanks to this arrangement, the side of the centrifugal device opposite to the drive shaft is free, enabling the lateral insertion of cup or bowl 2 and the installation of tubular component 9. This permits easy access to centrifugation cup or bowl 2 and its easy installation and removal.

Drive shaft 23 is mounted to pivot by means of two ball bearings 24, 25, respectively, integral to tray 22 and to top disk 26 located above cup or bowl 2. This top disk 26 is integral to drive shaft 27 of motor 28, coaxial to the rotating axis of rotor 1. The extremity of shaft 23 that extends above disk 26 is integral with a satellite pinion 29 engaged with a stationary pinion 30. The ratio between the diameters of satellite pinion 29 and of stationary pinion 30 is 1/1 so that if the rotation speed of tray 26 is $\omega$, that of shaft 23 around its axis is $2\omega$. The bottom extremity of this shaft 23 carries a notched pinion 31 connected by a notched belt 32 to a notched pinion 33, of the same diameter as notched pinion 31, so that rotor 1 is driven at speed $2\omega$.

Flexible tubular component 9 forms an open loop of which one extremity 9a is stationary and coaxial with the pivoting axis of rotor 1. This extremity 9a is fixed and held in a tubular connecting housing 10' similar to housing 10 that supports the other extremity of this tubular component 9. Each of these tubular components 10 and 10' shows a type of funnel 10a and 10'a respectively (FIG. 5) that provides support to this portion of tubular component 9 when it is subjected to the centrifugal force. This loop passes through an opening 22a in tray 22, so that it is driven around the pivoting axis of rotor 1 at speed $\omega$, while its extremity attached to the center of cup or bowl 2 is driven at speed $2\omega$ and while the other extremity 9a is stationary, so that the flexible component is driven between these two extremities at the speed—$\omega$ around its longitudinal axis while eliminating any torsion accumulation between these two extremities. This principle is well known since U.S. Pat. No. 3,586,413 by Adams. A support surface 22b integral with tray 22 serves to limit the deformation of tubular component 9 under the effect of the centrifugal force. The guiding parts of tubular component 9 are preferably made of a self-lubricating material or one with a slow friction coefficient, such as Oilamid®, bronze Teflon® or Valflon®.

Downstream from stationary component 9a of tubular component 9, the three tubes 4a, 5a and 6a separate and plasma tube 6a is connected to a flow regulating valve 34 according to the position of the surface of separation between the plasma and the blood cells in separation enclosure 3.

For that purpose, a double prism 3a is installed at the top extremity of separation enclosure 3 and consists of one piece with top part 2b of cup or bowl 2 during its injection. The portion of this double prism 3a that is covered with blood cells separated from the blood by the centrifugal force as a result of rotating cup or bowl 2 is opaque, while the part that emerges from the plasma is transparent. An optical device 35 comprising a laser and a photoelectric detector is installed with respect to this prism 3a, so that the photoelectric detector receives light reflected by the part of the double prism 3a that emerges from the transparent plasma. With each turn of cup or bowl 2, a signal of duration proportional to the angular value of the transparent zone of the double prism 3a is thus provided to an amplifier 36 for which the output is connected to proportional valve 34. According to the fact that this transparent zone increases or diminishes, amplifier 36 shall control proportional valve 34 so that it reduces or increases the section of tube 6a that evacuates the plasma, permitting it to maintain the balance between the flows in the outgoing tubes 5a and 6a through this adjustment, this on the basis of an incoming flow determined by the pump supplying blood in tube 4a, itself determined by the vein pressure in the donor's arm.

Sizing of centrifugation cup or bowl 2 and of tubular component 9 forming the open loop is selected to permit reducing the overall dimension, weight, price and volume for this cup or bowl 2 as for the whole centrifugal device for which sizing is essentially dependent on the diameter of the centrifugation cup or bowl. If the diameter diminishes, speed must be increased. The speed increase can be limited by increasing the height of the centrifuge enclosure 3, so that the maximum flow remains practically constant, the latter being determined by obtaining a good sedimentation of the blood cells.

As an example, the diameter of the cup or bowl is 80 mm and its height is essentially equal to its radius. Such a diameter corresponds approximately to one-third of that of the state-of-the-art separation rotors. Consequently, the length of the open loop formed by tube 9 corresponds essentially to one-third of the loops provided by the state-of-the-art.

By reducing the radius of cup or bowl 2 and thus the length of the loop formed by tube 9, the traction force exerted on it by the centrifugal force to which it is subjected can be maintained at a constant value. Instead of using three tubes of 4 mm in diameter, we have a single tube 9 of 7 mm in diameter, so that the resulting cross-sectional surface area is the same, namely 0.38 cm$^2$. The material of this tube is plastified PVC or silicone with a specific weight of 1.2 g/cm$^3$, as for the state-of-the-art. Since the length of the open loop of tubular component 9 is reduced to one-third of that of the state-of-the-art, the weight of this tubular component thus also corresponds considerably to one-third. Also, the radius of the open loop is reduced to one-third.

Traction force F exercised on this tube is equal to:

$$F=m\omega^2.R$$

For the state-of-the-art, one obtains at a loop speed of 1000 rpm ($\omega$=100), equal to half the rotor speed that is 2000 rpm and with a loop radius of 0.13 m, a force of:

$$F=0.014.100^2.0.13=18.2N$$

In the case of this example according to this, invention, with a weight of 0.0046 kg, a loop speed of 3000 rpm (equal to the speed of rotor 1 of 6000 rpm) and a loop radius of 0.045 m, the force is:

$$F=0.0046.300^2.0,045=18.6N$$

The value of the traction efforts is:

$$\sigma=F/S=18/38=0.47N/mm^2$$

Since the value of the alternate bending stresses on the tubular component is:

$$\sigma=E.r/R$$

where r=the radius of the tubular component
and R=the radius of the loop formed by this tubular component Since radius R is smaller in the case of this invention, in order to reduce $\sigma$, r and E must be reduced. In the example given, E=4 N/mm$^2$ and $\sigma_{breaking}$=12 N/mm$^2$. In the case of bending stresses equal to 1 million alternated bends, or 5½ hours of operation, this value is reduced by a factor of 5 to take into account additional fatigue, so that $\sigma_{breaking}$, for an alternated bending stress of 2.4 N/mm$^2$ $$\sigma=4.3,5/30=0.47N/mm^2$$

being a safety factor of 2.4/0.47≡5.

This example of sizing shows that it is quite possible to reduce very considerably the diameter of the separation enclosure without losing performance and without increasing stresses provided certain measures are taken for that purpose. However, this reduction in diameter permits reducing the size of the device in a very considerable way. This permits use of a much more compact device, that is lighter and less costly to manufacture. Since this device takes up little space, a greater number of devices can be installed on one and the same surface, which is important, such as in the case of trucks used for collecting plasma and where space is limited.

As an example, the rotating part according to the invention weighs 600 g while the rotors of the devices according to the state of the art weigh almost five times as much. That is the reason why for collecting blood, plasmapheresis is generally not conducted at the spot but blood is collected in flexible pouches that are then placed in very large centrifuges. In this case, erythrocytes can no longer be returned to the blood donor. However, the time required for the body to reproduce the quantity of erythrocytes is long which explains why several months are necessarily required in between two sessions of giving blood by the same donor, which would not be required if the erythrocytes could have been reinjected after separation. However, this is possible only if separation takes place simultaneously while the blood is taken.

There are other types of machines that operate with a single usage centrifugation bowl, but these require a rotating joint, leading to a more expensive solution that does not permit the simultaneous supply of the liquid to be centrifuged and the evacuation of the separated components, so that it is necessary to alternate the supply and the evacuation, resulting in a large extra-corporal volume.

The importance of having light and small centrifugal devices and, above all, disposable separation enclosures that can be produced cheaply, is consequently obvious. The ease of exchanging these enclosures or separation cups is consequently also a requirement Only when all of these conditions exist, can the replacement of the present methods used for collecting plasma be possible.

Another important aspect of this invention can be found in the fact that the complete liquid circulation is obtained by the overpressure with which the blood is brought into centrifugal cup or bowl 2. This overpressure must compensate the load losses induced in supply tube 4a, as well as in the recovery tubes of blood cells 5a and plasma 6a. To create such an overpressure, one can favorably use a peristaltic pump, for the purpose of ensuring the desired flow rate downstream of the separation. No peristaltic intake pump of outgoing components is consequently necessary since regulation of the plasma flow is obtained by regulating valve 34 controlled by its automatic control system on the basis of the position variation of the border between plasma and blood cells.

It is well understood that if this device is particularly appropriate for use in conducting plasmapheresis in line with the taking of blood, it can of course also be used in therapeutic applications. Indeed, one can observe that tubular component 9 containing the three tubes 4a, 5a and 6a is configured with a safety factor of 5 for continuous use exceeding 5 hours which permits its use in all applications considered.

The device covered by this invention can also be used for cleaning blood cells by introducing alternatively, the cells to be washed and a cleansing fluid, using the proper equipment known in this field. As a variant, the cleansing fluid could be introduced through an additional tube, thus permitting the simultaneous separation and cleaning. In this case, tubular component 9 shall then include four tubes instead of the three shown.

Figure 5:
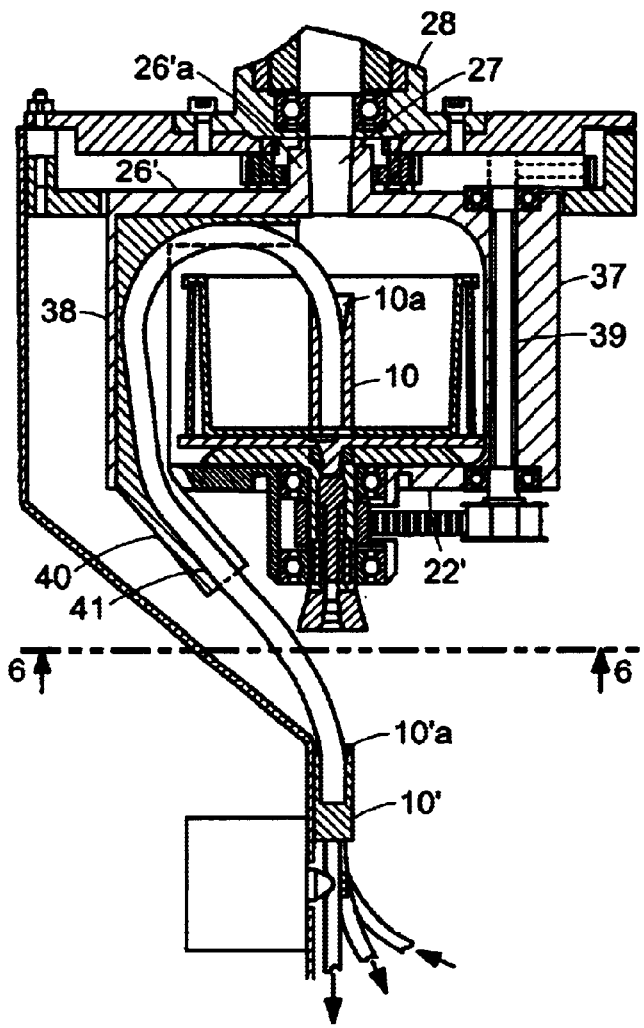
FIG. 5 is a partial sectional view of a variant of the form of execution of FIG. 1.
Figure 6:
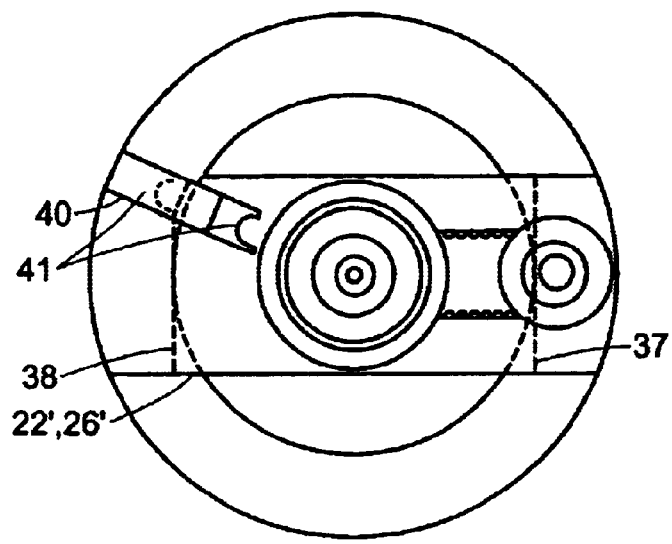
FIG. 6 is a view according to line VI—VI of FIG. 5.

For the variant illustrated by FIGS. 5 and 6, the two disks 22 and 26 of the previous form of execution are replaced by two diametrical arms 22', 26' that are made of a single aluminum piece with two diametrically opposite pillars 37 and 38. Arm 26' shows a hub 26'*a* that is pressed onto shaft 27 of motor 28. Pillar 37 shows a cylindrical passage 39 for the passage of drive shaft 23. The other pillar 38 is integral to a support 40 that has a guiding groove 41 of the tubular component 9.

Support 40 is designed to support flexible tubular component 9 in the area where its radius is the greatest, in other words, where the centrifugal force is the greatest. Funnel 10*a* supports the central part of tubular component 9.

To reduce friction between groove 41 of support 40 and tubular component 9 during the rotation of the device, support 40 is made, like support 22*b* in the form of execution of FIG. 1, of a material with a low friction coefficient. Besides the materials already mentioned, a polyethylene with high molecular weight (PEHMW) could be used. Sliding can also be improved by use during the manufacture of tubular component 9, when the latter is made of PVC, a silicon-based plastifying agent which makes its surface slide better. Friction can also be reduced by reducing the contact surface of groove 41 by streaks possibly in the form of corkscrews.

Figure 7:
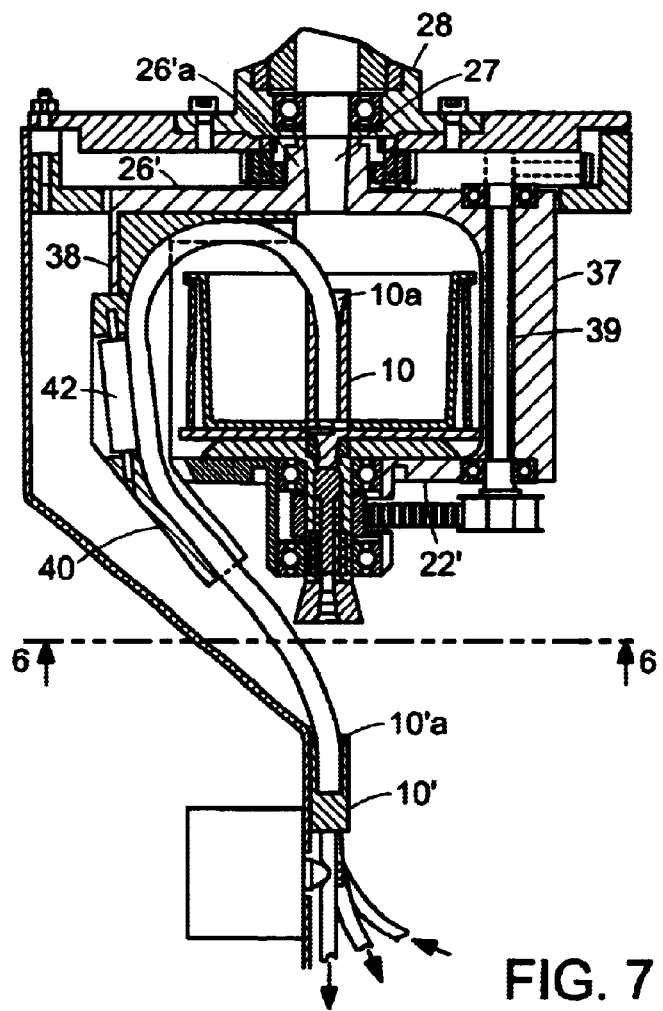
FIG. 7 is a similar view of FIGS. 1 and 5 of another variant.

According to a last variant illustrated by FIG. 7, in the groove of support 40 there are rollers 42 turning freely around axes that are parallel to that of tubular component 9. These rollers 42 are driven by the rotation of tubular component 9 on itself.

The rest of the centrifugal device coincides with the form of execution described before. The variant described in relation to FIGS. 5 and 6 facilitates the balance and permits increasing the safety of the device when it rotates at centrifugal speed. It also improves guidance and support of tubular component 9, which is as such minimally subjected to the centrifugal force.

What is claimed is:

1. A centrifugal device for liquids containing suspended particles, such as blood, comprising:
    a centrifugal unit with a center and a rotation axis;
    a peripheral separation chamber;
    a plurality of channels connecting the center of the centrifugal unit to said separation chamber, each channel having a central extremity;
    a plurality of tubes having first and second extremities, the central extremities of the respective channels attached to the first extremities of the tubes and the second extremities of the tubes being angularly stationary and coaxially located with respect to the rotating axis;
    first drive units to turn the tubes around said rotating axis at an angular speed $\omega$; and
    second drive units to turn the centrifugal unit around said rotating axis at an angular speed $2\omega$ wherein the centrifugal unit has a radius between 25 and 50 mm and a height between 75 and 125% of the radius.

2. A centrifugal device according to claim 1, wherein the centrifugal unit is capable of rotating at an angular speed $2\omega > 500$ rad/sec.

3. A centrifugal device according to claim 1, wherein a liquid introduced to the centrifugal unit is capable of flowing at a rate of less than 100 mL/min.

4. A centrifugal device according to claim 1, wherein:
    said tubes are capable of withstanding a traction force of <0.7 N/mm$^2$;
    an elasticity module for the tubes is <5 N/m$^2$; and
    a rupture strength for the tubes at alternate bending is higher than 1.5 N/mm $^2$.

5. A device according to claim 1, wherein said centrifugal device has the form of a bowl that includes a bottom part attached to a top part so as to form said separation chamber.

6. A device according to claim 1, wherein said tubes form open loops around the centrifugal unit and are incorporated in one flexible tubular component.

7. A device according to claim 6, wherein the diameter of a cross-section of said tubular component does not exceed 7 mm.

8. A device according to claim 7, wherein a cross-section of each of the tubes is elliptic and defines a large axis, with the large axes of the ellipses being tangential to at least a concentric circle to the longitudinal axis of said tubular component.

9. A device according to claim 6, wherein the device includes support devices to limit the deformation of said loops of the flexible tubular component under the effect of the centrifugal force.

10. A device according to claim 6, wherein friction between the tubular component and moving parts in contact therewith is reduced by the incorporation of a silicon-based plastifying agent onto the surface of the tubular component and/or by a reduction of the contact surface of the moving parts, wherein the contact surface is shaped in the form of corkscrews.

11. A device according to claim 1, wherein one of said tubes to be connected to a collector of one of the components coming from centrifugation includes:
    a proportional valve; and
    detection devices arranged upstream of the tube to measure the degree of purity of the component that has to flow through the tube, with the detector being connected to said proportional valve to regulate the flow rate in said tube according to said measured degree of purity.

12. A device according to claim 11, wherein a prism is installed in said separation chamber with said detection devices comprising a laser beam that is stationary with respect to said centrifugal unit and a photoelectric cell to measure the position of a border between the blood cells and the plasma and to deliver a signal characteristic of said position to a control unit of said proportional valve.

13. A device according to claim 1, wherein a space is provided laterally to the first and second drive units to permit passage of said centrifugal unit.

14. Use of a device according to claim 1, wherein:
    said liquid to be centrifuged is put under pressure (P) to produce a flow at a given rate;
    the degree of purity is measured for at least one of the centrifuged components; and
    the proportion of the respective flow rates is regulated for the two components coming from centrifugation according to said degree of purity.

15. A device according to claim 1, wherein the central extremities of the channels are integral with the first extremities of the tubes.

16. A centrifugal unit comprising a centrifugal component and a plurality of tubes, said unit to turn around an axis to separate the components of a liquid, blood in particular, with such plurality of tubes displaying a single tubular component wherein said unit includes:

a base in the form of a disk;

an external cylindrical wall extending from the base;

an internal cylindrical wall extending from the base and separated by the external wall so as to define a ring-shaped separation chamber among each other;

a tubular housing almost extending coaxially to said rotating axis from the base to receive an end of a tubular unit; and a plurality of channels extending radially in the base of the centrifugal unit, with each channel providing communication between a respective tube of the tubular unit and the separation chamber, with the centrifugal unit having a radius between 25 and 50 mm and a height between 75 and 125% of the radius.

17. A centrifugal unit according to claim 16, wherein each channel has a terminal point inside the separation chamber and each terminal point occupies a different radial position in the separation chamber so as to provide communication with a different component of the liquid to be separated.

18. A centrifugal unit according to claim 17, wherein the unit comprises a double prism installed in the separation chanber with the double prism working together with an optical device so as to detect a level of a chosen component in the separation chamber.

19. A centrifugal unit according to claim 18 wherein the double prism is installed in a portion of the separation chamber opposite the base.

20. A device to centrifuge a liquid containing suspended particles, blood in particular, wherein the device comprises:

a first drive component mounted to pivot around an axis;

a second drive component mounted to pivot coaxially with respect to the pivoting axis of said first drive;

devices to drive the first and second drive components at a 2:1 ratio;

a centrifugal unit coupled but removable to the first drive component having a tubular housing coaxially connected to the pivoting axis; further having a radius between 25 and 50 mm and a height between 75 and 125% of the radius;

a tubular connection housing; and a tubular component with a first extremity coupled to the tubular housing of the centrifugal unit and a second extremity coupled to the connecting tubular housing and defining an axis that is coaxially located to said pivoting axis such that the tubular component is joined at the second drive component to rotate and the tubular component further incorporating a plurality of tubes installed inside, with each tube having an elliptic cross-section to facilitate the rotation of the tubular component around the longitudinal axis.

21. A centrifugal device according to claim 20, wherein the elliptic cross-section of each tube defines a large axis and the large axes are tangential to at least a circle that is concentric with respect to the longitudinal axis of the tubular component.

22. A device according to claim 21, wherein the large axes of the elliptic tubes are tangential to a plurality of circles that are each concentric to the longitudinal axis of the tubular component.

* * * * *

(12) EX PARTE REEXAMINATION CERTIFICATE (7676th)

United States Patent
Rochat

(10) Number: US 6,705,983 C1
(45) Certificate Issued: Aug. 10, 2010

(54) COMPACT CENTRIFUGE DEVICE AND USE OF SAME

(75) Inventor: Jean-Denis Rochat, Genolier (CH)

(73) Assignee: Haemonetics Corporation, Braintree, MA (US)

Reexamination Request:
No. 90/010,741, Nov. 17, 2009

Reexamination Certificate for:
Patent No.: 6,705,983
Issued: Mar. 16, 2004
Appl. No.: 09/958,467
Filed: Jan. 17, 2002

(22) PCT Filed: Apr. 7, 2000
(86) PCT No.: PCT/IB00/00437
§ 371 (c)(1),
(2), (4) Date: Jan. 17, 2002
(87) PCT Pub. No.: WO00/61295
PCT Pub. Date: Oct. 19, 2000

(30) Foreign Application Priority Data

Apr. 9, 1999 (EP) .................................. 99810295

(51) Int. Cl.
*B04B 5/00* (2006.01)
*B04B 5/04* (2006.01)
*A61M 1/36* (2006.01)

(52) U.S. Cl. .................. 494/2; 494/10; 494/45
(58) Field of Classification Search ................. None
See application file for complete search history.

(56) References Cited

U.S. PATENT DOCUMENTS

| 3,519,201 A | 7/1970 | Eisel et al. |
| 3,707,354 A | 12/1972 | Goodman |
| 3,880,592 A | 4/1975 | Kelley et al. |
| 4,944,883 A | 7/1990 | Schoendorfer et al. |
| 5,431,814 A | 7/1995 | Jorgensen |
| 5,603,845 A | 2/1997 | Holm |
| 5,641,414 A | 6/1997 | Brown |
| 5,656,163 A | 8/1997 | Brown |
| 5,750,025 A | 5/1998 | Holmes et al. |
| 5,804,079 A | 9/1998 | Brown |

OTHER PUBLICATIONS

Richard I. Brown, *The Physics of Continuous Flow Centrifugal Cell Separation*, Artificial Organs, vol. 13, No. 1, pp. 4–20 (1989).

*Primary Examiner*—Terrence R Till

(57) ABSTRACT

This device includes a centrifugal cup or bowl (2) rotating at the speed of 2ω around its revolving axis, a separation chamber (3) connected to the center of this cup or bowl (3) by three channels (4, 5, 6) integral to three flexible tubes (4a, 5a, 6b) forming open loops driven at the speed of ω while their second respect extremities, coaxially located with respect to the first ones, are stationary. The radius and height of this cup or bowl (2) are between 25-50 mm, and 75 to 125% respectively of this radius; its angular speed 2ω is >500 rad/sec to ensure a flow rate for the liquid to be centrifuged of at least 100 ml/min. The material and the dimensions of the tubes (4a, 5a, 6a) are chosen so that the traction force exerted on them is <0.7 N/mm², its elasticity module is <5 N/mm² and its rupturing resistance to alternate bending is higher than 1.5 N/mm².

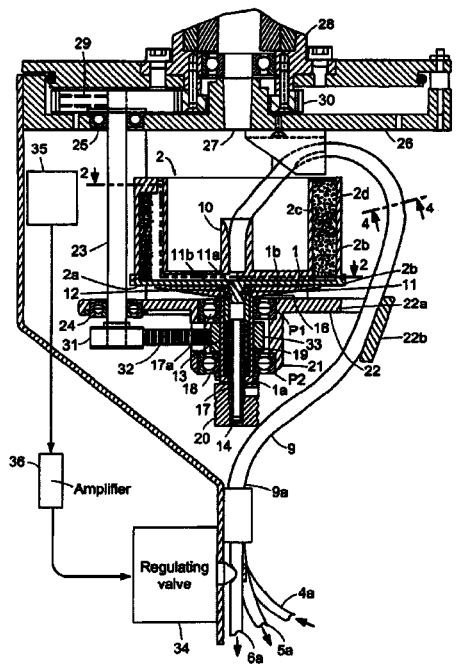

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claim 16 is confirmed.

Claims 1-15 and 17-22 were not reexamined.

\* \* \* \* \*